United States Patent [19]

Kasahara et al.

[11] Patent Number: 4,885,929
[45] Date of Patent: Dec. 12, 1989

[54] OZONE GAS SENSOR AND OZONE GAS DETECTING DEVICE HAVING OZONE GAS SENSOR

[75] Inventors: Riichiro Kasahara; Tadashi Takada, both of Osaka, Japan

[73] Assignee: New Cosmos Electric Co. Ltd., Osaka, Japan

[21] Appl. No.: 254,185

[22] Filed: Oct. 6, 1988

[30] Foreign Application Priority Data

Oct. 8, 1987 [JP] Japan .................................. 62-255477

[51] Int. Cl.⁴ .............................................. G01N 27/00
[52] U.S. Cl. ........................................... 73/23; 422/98
[58] Field of Search ................. 73/23, 27; 422/83, 98; 436/135; 338/34; 340/634; 357/21

[56] References Cited

U.S. PATENT DOCUMENTS

| | | | |
|---|---|---|---|
| 4,203,946 | 5/1980 | Ryerson | 73/27 R |
| 4,240,799 | 12/1980 | Ryerson | 73/27 R |
| 4,324,761 | 4/1982 | Harris | 422/98 |
| 4,343,768 | 8/1982 | Kimura | 422/98 |
| 4,580,439 | 4/1986 | Manaka | 73/23 |

OTHER PUBLICATIONS

Improvement on Output Decrease of Thin Film Type $O_3$ Gas Sensor Associated with Mixing of Interfering Gas Semi Conductor Type $O_3$ Semiconductor Type $O_3$ Sensor.

Sensor Ozone Sensor with the Use of Thin Films of Transition Metal Oxides.

*Primary Examiner*—Hezron E. Williams
*Attorney, Agent, or Firm*—Jones, Tullar & Cooper

[57] ABSTRACT

An ozone gas sensor comprising a film type semiconductor element including a substrate and a semiconductor film consisting of a metallic oxide formed on the substrate, and a layer of silica formed on a surface of the film type semiconductor element. At least one thin film layer of one or a plurality of types selected from metals and metal oxides is interposed between the semiconductor film and the layer of silica.

9 Claims, 5 Drawing Sheets (a)

(c)

(b)

(d)

OZONE GAS SENSOR AND OZONE GAS DETECTING DEVICE HAVING OZONE GAS SENSOR

BACKGROUND OF THE INVENTION (1) Field of the Invention

The present invention relates to an ozone gas sensor and an ozone gas detecting device having the ozone gas sensor.

(2) Description of the Prior Art

A conventional ozone gas sensor comprises a film type semiconductor element including an insulating substrate such as of alumina and a semiconductor film consisting of a metallic oxide formed on the substrate, and a layer of silica formed on a surface of the film type semiconductor element. The semiconductor film of a metallic oxide allows ozone gas having high reactivity to reach a sensing section of the sensor without decomposing on the surface of the semiconductor film. The layer of silica formed on the semiconductor element promotes sensitivity to ozone gas.

Such an ozone gas sensor has the following problem when used in the presence of both ozone gas and a reducing gas:

Where the film type semiconductor element comprises an n-type semiconductor, the resistance of the semiconductor increases through contact with ozone gas and decreases through contact with the reducing gas, thereby rendering measurement results inaccurate. Conversely, where the film type semiconductor element comprises a p-type semiconductor, the resistance of the semiconductor decreases through contact with ozone gas and increases through contact with the reducing gas. In either case, measurement results are inaccurate, being lower than actual levels or dispersed.

Consequently, an ozone gas detecting device incorporating such an ozone gas sensor has low sensitivity and precision in the presence of a reduction gas.

SUMMARY OF THE INVENTION

Having regard to the state of the art noted above, an object of the present invention is to provide an ozone gas sensor which is easy to handle, inexpensive, and capable of measuring ozone gas with high sensitivity even where ozone gas and a reducing gas coexist.

In order to achieve the above object, an ozone gas sensor according to the present invention comprises a film type semiconductor element including a substrate and a semiconductor film consisting of a metallic oxide formed on the substrate, and a layer of silica formed on a surface of the film type semiconductor element, wherein at least one thin film layer of one or a plurality of types selected from metals and metal oxides is interposed between the semiconductor film and the layer of silica.

At least one thin film layer of one or a plurality of types selected from metals and metal oxides interposed between the semiconductor film and the layer of silica is effective to prevent a substantial reduction in the sensor output responsive to ozone gas in the presence also of a reducing gas.

The thin film layer or layers may be formed between the semiconductor film and the layer of silica by an ordinary film forming technique without requiring a special technique or an expensive apparatus.

The present invention thus provides an ozone gas sensor easy to handle, inexpensive and capable of high-sensitivity and high-precision measurement.

An ozone gas detecting apparatus incorporating this ozone gas sensor is also easy to handle, inexpensive and highly sensitive.

Other advantages of the present invention will be apparent from the detailed description of the preferred embodiments to follow.

BRIEF DESCRIPTION OF THE DRAWINGS

The drawings illustrate ozone gas sensors and ozone gas detecting devices having these ozone gas sensors according to the present invention, in which.

DETAILED DESCRIPTION OF THE PREFERRED EMBODIMENTS

Ozone gas sensors and ozone gas detecting devices having the ozone gas sensors according to the present invention will be described in detail hereinafter with reference to the drawings.

Figure 1:
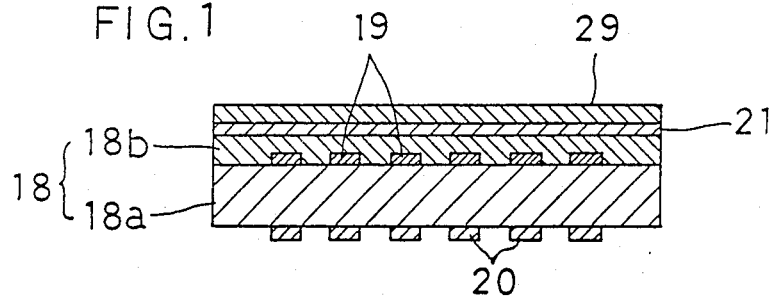
FIG. 1 is a schematic sectional view showing the principle of a semiconductor type ozone gas sensor.

FIG. 1 is a schematic sectional view of a semiconductor film type ozone gas sensor. This sensor comprises a film type semiconductor element 18, a thin film layer 21 formed on the semiconductor element 18, and a layer of silica ($SiO_2$) 29 formed on the thin film layer 21.

The semiconductor element 18 may comprise an insulating substrate 18a consisting of alumina or the like, and a semiconductor film 18b formed on the substrate 18a and including indium oxide ($In_2O_3$), tin oxide ($SnO_2$), zinc oxide (ZnO) or other metallic oxide as a main component thereof. The thin film layer 21 comprises a single layer or a plurality of layers of one or different types selected from metals and metallic oxides. The metals available for use include palladium, platinum and the like, while the metallic oxides include oxides of chromium, manganese, iron, cobalt, palladium, platinum, copper and other transition metals. The thin film layer 21 may have a single layer or multilayer construction comprising a combination of a metal and an oxide similar thereto, a combination of a metal and an oxide dissimilar thereto, or comprising a single metal or a plurality of metals, or a single metallic oxide or a plurality of metallic oxides. The thin film layer 21 may be formed on the film type semiconductor element 18 by the thermal decomposition, chemical deposition, physical deposition or other method used for forming a metal compound or compounds into a film.

A layer of silica 29 is formed on the thin film layer 21 as noted above. This layer 29 is formed by chemically depositing an organic silicon compound such as hexamethyl disiloxane on the thin film layer 21.

Number 19 in FIG. 1 indicates a comb-shaped electrode embedded between the insulating substrate 18a and semiconductor film 18b, and number 20 indicates a heater attached to a back surface of the insulating substrate 18a.

Sensor output variations occurring in the presence of both ozone gas and ethyl alcohol gas which is a reducing gas will be described next. FIG. 2(a) through 2(d) schematically show response waveforms and reductions in the ozone gas sensitivity of various ozone gas sensors described below, in the coexistence of ozone gas and ethyl alcohol gas. The sections marked by |←  →| in these drawings represent the coexistence of ozone gas and ethyl alcohol gas.

Figure 2:
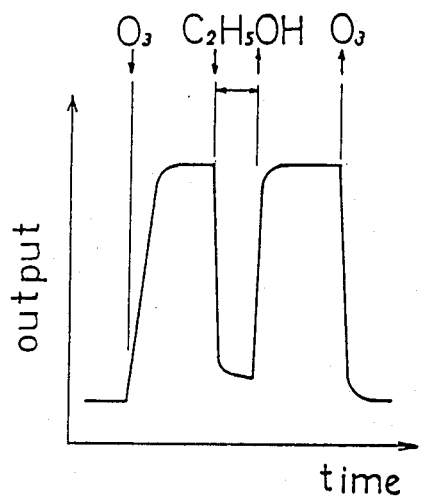
FIG. 2(a) through 2(d) are graphs showing response waveforms and output reductions of various ozone gas sensors in the presence of both ozone gas and ethyl alcohol gas.
Figure 2:
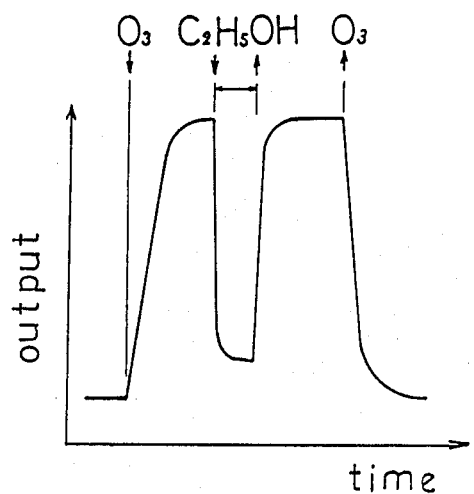
Figure 2:
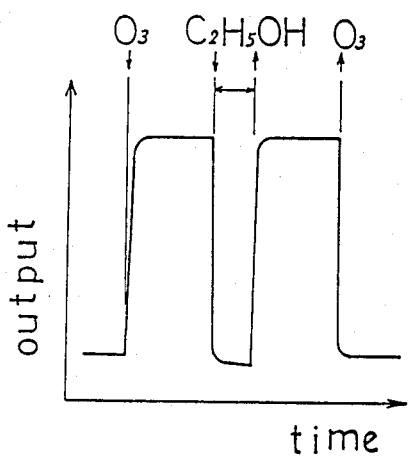
Figure 2:
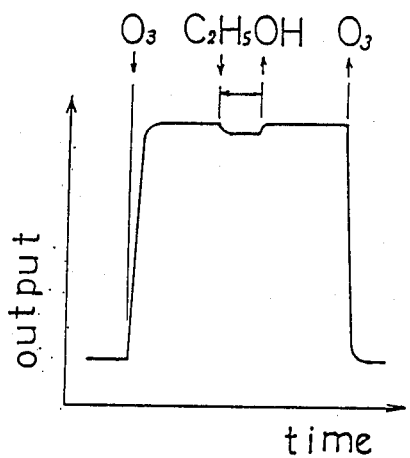

FIG. 2(a) shows the case of using an ordinary ozone gas sensor having the metallic oxide semiconductor film 18b formed on the insulating substrate 18a. FIG. 2(b) shows the case of using a sensor having the thin film layer 21 of a metallic oxide formed on the film type semiconductor element 18. FIG. 2(c) shows the case of using a sensor having the layer of silica 29 formed on the film type semiconductor element 18. FIG. 2(d) shows the case of using the film type ozone gas sensor according to this embodiment.

It will be seen that the sensor output deteriorates in the coexistence of ozone gas and ethyl alcohol gas where the thin film layer of a metallic oxide is formed (FIG. 2(b)) on the ordinary film type semiconductor element (FIG. 2(a)). Where the layer of wilica is formed (FIG. 2(c)) on the ordinary film type semiconductor element (FIG. 2(a)), the sensor output increases in the absence of ethyl alcohol gas but no significant improvement is seen as regards the output in the coexistence of ozone gas and ethyl alcohol gas. By contrast, the ozone gas sensor according to this embodiment (FIG. 2(d)) shows a great improvement with respect to the output reduction in the coexistence of ozone gas and ethyl alcohol gas. It has thus been confirmed that, by interposing the thin film layer of a metallic oxide between the film type semiconductor element and the layer of silica, the output reduction is effectively checked in the coexistence of the two gases while substantially sustaining the sensor output responsive to ozone gas in the absence of ethyl alcohol gas.

The present invention will particularly be described next with reference to experiments conducted.

[EXPERIMENT 1]

Film type ozone gas sensors were manufactured, each of which comprised a film type semiconductor element having indium oxide as the main component thereof and prepared by the vacuum deposition method, and a thin film layer or layers of a metallic oxide, different metallic oxides or a metal and metallic oxide combination formed on the semiconductor element. The thin film layer was formed by applying to the semiconductor element a metallic salt solution of one of the metals listed in Table 1 below, and drying and baking the product. Each sensor further comprised a layer of silica formed by chemically depositing hexamethyl disiloxane on the thin film layer.

Each ozone gas sensor thus manufactured was exposed to a mixture of ozone gas and ethyl alcohol gas to measure the normalized sensor output responsive to ozone gas. Results of the measurement are shown in the righthand column of Table 1. The results confirm that the sensors according to this invention employing any one or more of the listed metals and their oxides are effective for checking the output reduction in the presence of a reducing gas.

TABLE 1

| Metallic Oxide Layers | Sensor Output in $O_3$ and $C_2H_5OH$ |
| --- | --- |
| Cr Oxide | 0.23 |
| Mn Oxide | 0.72 |
| Fe Oxide | 0.68 |
| Co Oxide | 0.90 |
| Pd and/or Pd Oxide | 0.30 |
| Pt and/or Pd Oxide | 0.49 |
| Cu Oxide | 0.91 |
| Ce Oxide | 0.49 |
| (Co + Cu) Oxide | 0.95 |
| Ce Oxide Layer + Fe Oxide Layer | 0.70 |
| None | 0.13 |

[EXPERIMENT 2]

Film type ozone gas sensors were manufactured, each of which comprised a film type semiconductor element having tin oxide as the main component thereof and prepared by the vacuum deposition method, and a thin film layer or layers of a metallic oxide, different metallic oxides or a metal and metallic oxide combination formed on the semiconductor element. The thin film layer was formed by applying to the semiconductor element a metallic salt solution of one of the metals listed in Table 2 below, and drying and baking the product. Each sensor further comprised a layer of silica formed by chemically depositing hexamethyl disiloxane on the thin film layer.

Each ozone gas sensor thus manufactured was exposed to a mixture of ozone gas and ethyl alcohol gas to measure the normalized sensor output responsive to ozone gas. Results of the measurement are shown in the righthand column of Table 2. The results confirm that these sensors are also effective, by virtue of the thin film layer, for checking the output reduction in the presence of a reducing gas although slightly less effective than in Experiment 1.

TABLE 2

| Metallic Oxide Layers | Sensor Output in $O_3$ and $C_2H_5OH$ |
| --- | --- |
| Cr Oxide | 0.17 |
| Mn Oxide | 0.68 |
| Fe Oxide | 0.65 |
| Co Oxide | 0.87 |
| Pd and/or Pd Oxide | 0.35 |
| Pt and/or Pd Oxide | 0.54 |
| Cu Oxide | 0.87 |
| Ce Oxide | 0.44 |
| (Co + Cu) Oxide | 0.93 |
| Ce Oxide Layer + Fe Oxide Layer | 0.65 |

TABLE 2-continued

| Metallic Oxide Layers | Sensor Output in $O_3$ and $C_2H_5OH$ |
|---|---|
| None | 0.11 |

[EXPERIMENT 3]

Film type ozone gas sensors were manufactured, each of which comprised a film type semiconductor element having zinc oxide as the main component thereof and prepared by the vacuum deposition method, and a thin film layer or layers of a metallic oxide, different metallic oxides or a metal and metallic oxide combination formed on the semiconductor element. The thin film layer was formed by applying to the semiconductor element a metallic salt solution of one of the metals listed in Table 3 below, and drying and baking the product. Each sensor further comprised a layer of silica formed by chemically depositing hexamethyl disiloxane on the thin film layer.

Each ozone gas sensor thus manufactured was exposed to a mixture of ozone gas and ethyl alcohol gas to measure the normalized sensor output responsive to ozone gas. Results of the measurement are shown in the righthand column of Table 3. The results confirm that these sensors are also effective, by virtue of the thin film layer, for checking the output reduction in the presence of a reducing gas although slightly less effective than in Experiment 1.

TABLE 3

| Metallic Oxide Layers | Sensor Output in $O_3$ and $CH_2H_5OH$ |
|---|---|
| Cr Oxide | 0.20 |
| Mn Oxide | 0.75 |
| Fe Oxide | 0.65 |
| Co Oxide | 0.85 |
| Pd and/or Pd Oxide | 0.34 |
| Pt and/or Pd Oxide | 0.50 |
| Cu Oxide | 0.90 |
| Ce Oxide | 0.51 |
| (Co + Cu) Oxide | 0.91 |
| Ce Oxide Layer + Fe Oxide Layer | 0.71 |
| None | 0.12 |

Ozone gas sensors according to other embodiments of the invention will be described next.

Figure 3:
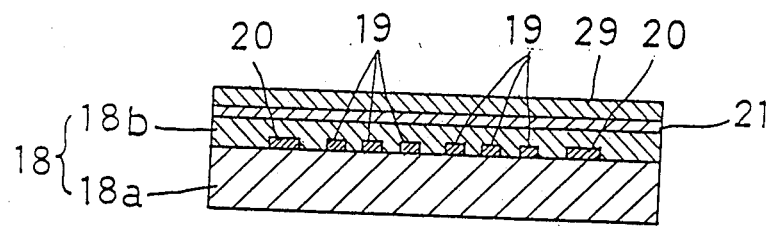
FIG. 3 is a sectional view of a semiconductor type ozone gas sensor according to another embodiment of the invention.

As shown in FIG. 3, the comb-shaped electrode 19 and the heater 20 may be formed on the same surface of the insulating substrate 18a, the electrode 19 being covered by the semiconductor film 18b formed on the substrate 18a. The heater 20 may be embedded in the substrate 18c.

Figure 4:
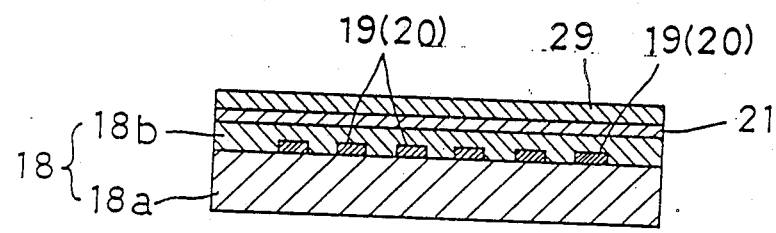
FIG. 4 is a sectional view of a semiconductor type ozone gas sensor according to a further embodiment of the invention.

As shown in FIG. 4, an electrode 19 acting also as a heater 20 may be formed on the insulating substrate 18a, with the semiconductor film 18b formed on the substrate 18a to cover the electrode 19.

Figure 5:
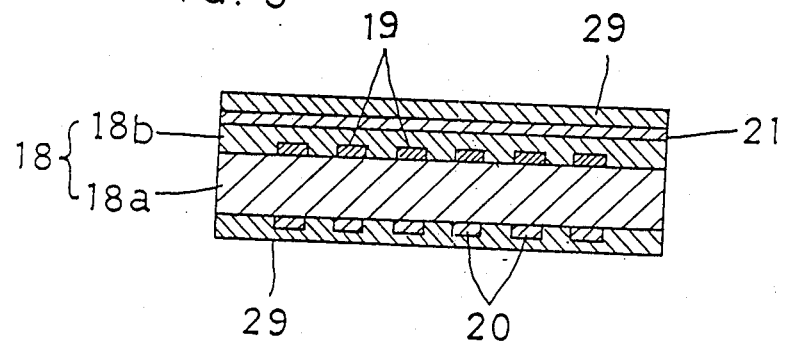
FIG. 5 is a sectional view of a semiconductor type ozone gas sensor according to a still further embodiment of the invention.

As shown in FIG. 5, an additional layer of silica 29 may be formed on the back surface of the insulating substrate 18a so as to cover the heater 20. This construction, in addition to the foregoing advantages, is effective, by means of the additional layer of silica 29, to enclose surfaces of the heater 20 out of contact with air and thus providing a protection for the heater 20. This heater 20 will retain stable heating characteristics over a long period of use, and promote long-term reliability of the thin film type ozone gas sensor.

In the above embodiments, the thin film layer is interposed as a uniform layer between the film type semiconductor element and the layer of silica. This thin film layer, however, may comprise a non-uniform layer with a metal or metallic oxide dispersed in high concentration, for example. Further, while the foregoing embodiments have been described in relation to ethyl alcohol gas as an example of reducing gas which affects the sensor output responsive to ozone gas to the greatest extent, the ozone gas sensors according to the present invention will produce the same effects in the presence of other reducing gases such as hydrogen, ammonia and methane gases.

The semiconductor film formed on the substrate in the described semiconductor type gas sensors may comprise a metallic oxide having tin oxide ($SnO_2$), zinc oxide (ZnO) or ferric oxide ($Fe_2O_3$) as a main component. Further, the semiconductor film may comprise indium oxide ($In_2O_3$) included in at least one of the above metallic oxides, or have indium oxide as the main component. The semiconductor film having indium oxide as the main component in prticular has high selectivity with respect to ozone gas ($O_3$).

Figure 7:
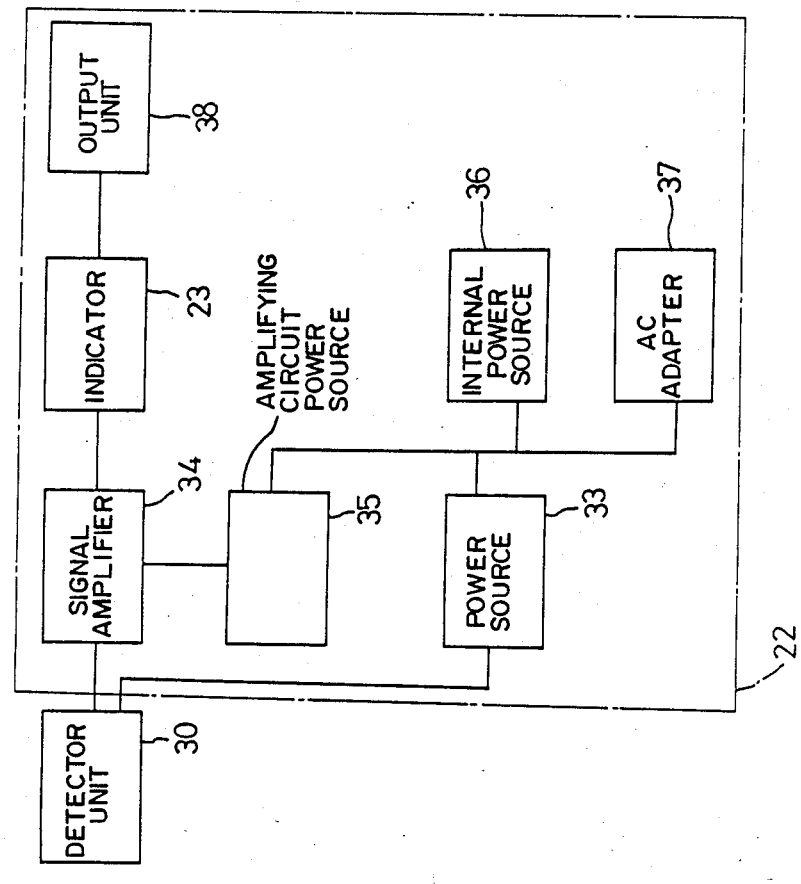
FIG. 7 is a block diagram showing a constructional outline of the ozone gas detecting device shown in FIG. 6.
Figure 6:
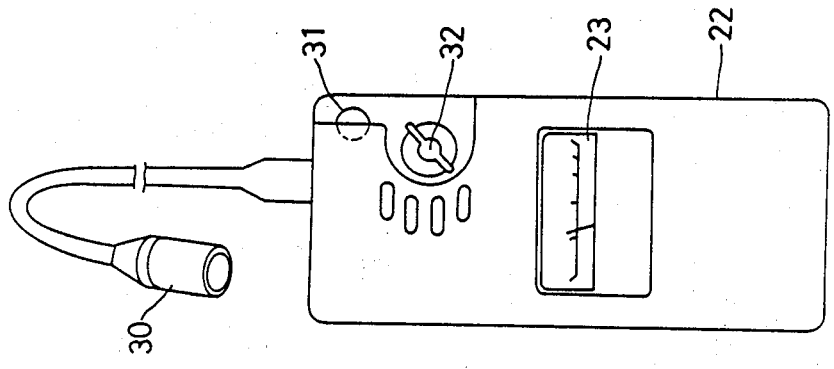
FIG. 6 is a front view of an entire ozone gas detecting device.

FIGS. 6 and 7 illustrate an ozone gas detecting device having one of the described ozone gas sensors according to the present invention.

This detecting device comprises a detector unit 30 containing an ozone gas sensor 7, and a casing 22 including an indicator 23 for providing a visual display of measurement results, a zero adjuster knob 31 and a mode changeover switch 32 for varying measuring magnification. The casing 22 houses a power source 33 for electrifying the heater of the ozone gas sensor 7 in the detector unit 30, a signal amplifier 34 for amplifying a signal received from the detector unit 30, an amplifying circuit power source 35 for driving the signal amplifier 34, an internal power source 36 and an AC adapter 37 for supplying power to the amplifying circuit power source 35 and the heater power source 33, and an output unit 38 for outputting data to be displayed by the indicator 23 and to be recorded by a recorder and for giving an alarm. The alarm may be given by a buzzer or a flashing color lamp when ozone gas concentration exceeds a predetermined level or falls below a predetermined level or to zero. The indicator 23 includes a control signal output circuit. The internal power source 36 normally comprises a battery. Either one or both of the internal power source 36 and AC adapter 37 may be provided. Although not shown, a source switch for operating the detecting device is provided on an outer wall of the casing 22, and a battery lamp for indicating a battery operation and an output terminal may also be provided as appropriate.

Another example of ozone gas detecting device will be described next with reference to FIGS. 8 through 11.

Figure 8:
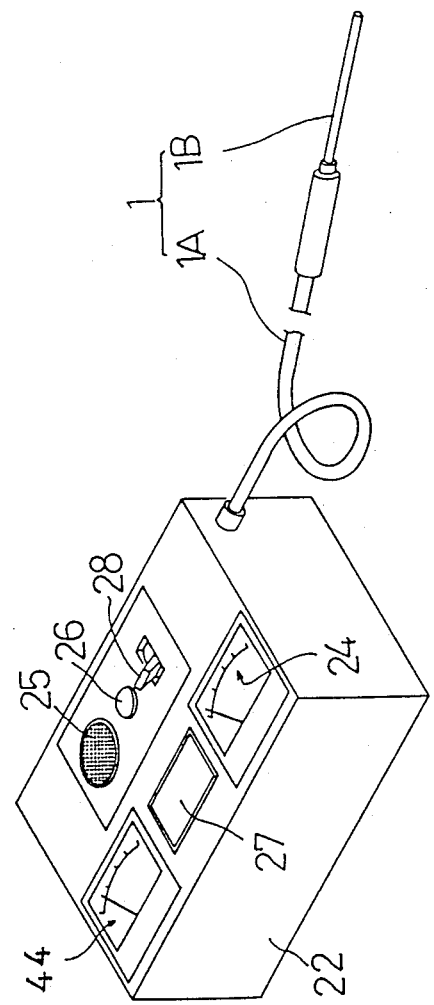
FIG. 8 is a perspective view of a modified ozone gas detecting device.

This detecting device is a suction type device and comprises a casing 22' including, as shown in FIG. 8, a first indicator 44 associated with an ozone gas measuring sensor 5, a second indicator 24 associated with an ozone gas removal confirming sensor 7', an alarm buzzer 25 and an alarm lamp 26 operable through an automatic control unit 9, a recovery section 27 of a catalyzer 6, and a source switch 28. A gas intake tube 1 extends from the casing 22, which intake tube 1 includes a flexible Teflon tube 1A and a stainless steel tube 1B connected to a distal end of the Teflon tube 1A. The ozone gas measuring sensor 5 is mounted on a gas intake passage R for detecting ozone gas concentration in the gas drawn through the gas intake tube 1. The gas intake passage R communicates with an intake port 4 of an electric suction pump 3 having a gas exhaust port 2 opening to the ambient. The stainless steel tube 1B may be replaced with a Teflon tube.

Figure 9:
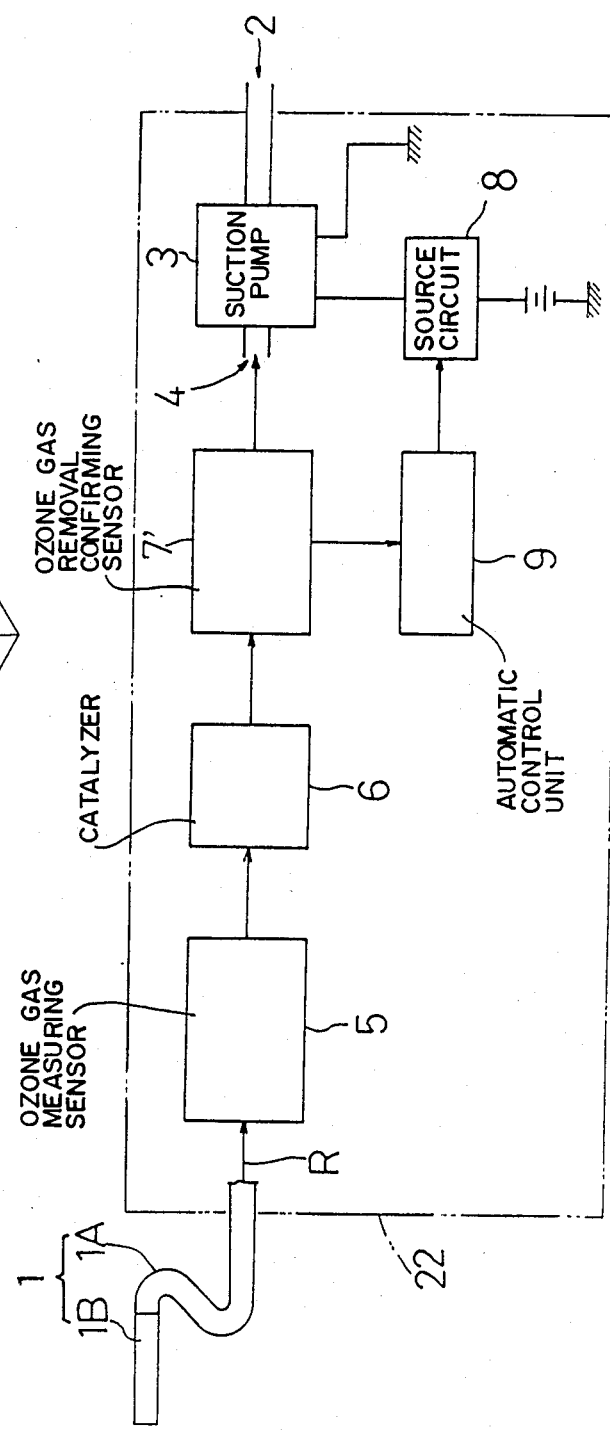
FIG. 9 is a block diagram showing a constructional outline of the ozone gas detecting device shown in FIG. 8.

As shown in outline in FIG. 9, the gas intake passage R includes the catalyzer 6 disposed between the ozone gas measuring sensor 5 and the suction pump 3 for reducing ozone gas to oxygen gas, and the ozone gas removal confirming sensor 7' disposed between the catalyzer 6 and the suction pump 3. The automatic control unit 9 is operable to automatically turn off a source circuit 8 connected to the suction pump 3 only when the ozone gas removal confirming sensor 7' gives a detection result that the ozone gas concentration in the gas having passed through the catalyzer 6 exceeds a predetermined level. Instead of the construction for causing the automatic control unit 9 to automatically turn off the source circuit 8 connected to the suction pump 3, a valve may be provided on the intake passage R upstream of the suction pump 3 for stopping the gas flow to the suction pump 3, the valve being automatically closed when the ozone gas concentration in the gas having passed through the catalyzer 6 exceeds the predetermined level.

The gas intake tube 1 may include a filter formed of alumina silicate at an inlet thereof for removing gases and other matters obstructive to the measurement.

Figure 11:
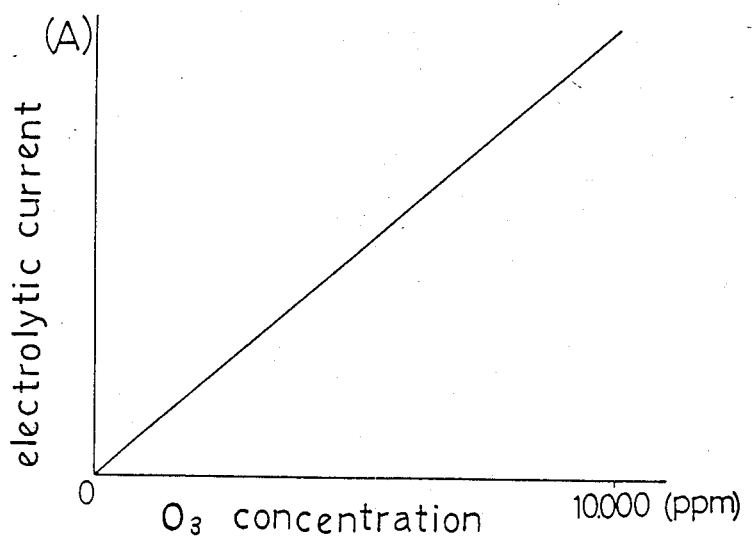
FIG. 11 is a graph showing output variations of the potentiostatic electrolysis type ozone gas sensor shown in FIG. 10.

The ozone gas measuring sensor 5 may be the potentiostatic electrolysis type, or may be the semiconductor type as illustrated in FIGS. 1 and 3–5. The gas sensor of the potentiostatic electrolysis type, as shown in FIG. 11, is capable of detecting ozone gas over a wide concentration range and is particularly effective for detecting high concentration ozone gas. On the other hand, the semiconductor type gas sensor is capable of detecting low concentration ozone gas with high sensitivity.

Figure 10:
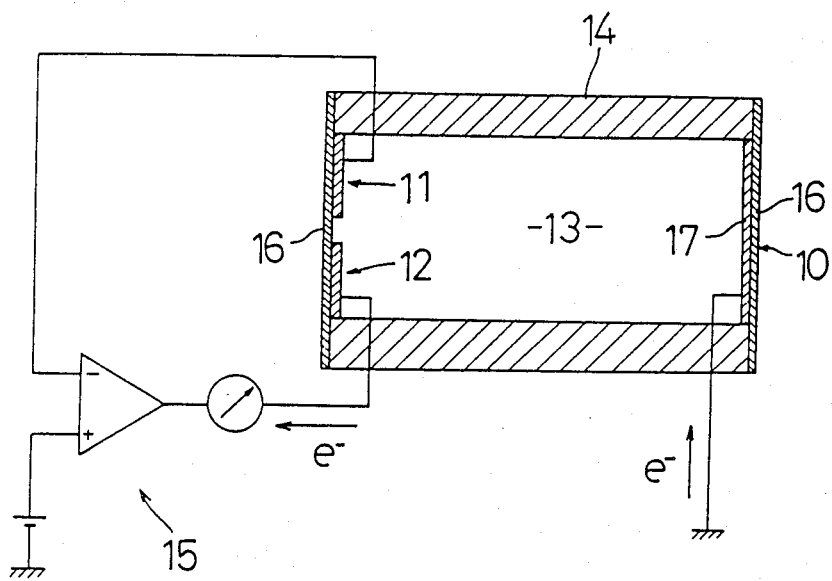
FIG. 10 is a view showing the principle of an ozone gas sensor of the potentiostatic electrolysis type which is one example of ozone gas sensor incorporated into the ozone gas detecting device shown in FIG. 8.

The potentiostatic electrolysis type gas sensor 5, as its principle is shown in FIG. 10, comprises a working electrode 10, a reference electrode 11, a counter electrode 12, an electrolytic cell 14 filled with an electrolyte 13, and a potentiostat circuit 15. Each of the electrodes 10, 11 and 12 comprises a gas-permeable membrane 16 such as Teflon (PTFE) coated with a noble metal catalyst. The electrolyte 13 comprises an acid solution. The electrolytic cell 14 is formed of a plastic having high chemical resistance, such as vinyl chloride.

Ozone gas having penetrated the gas-permeable membrane 16 is reduced on a catalyst layer 17 of the working electrode 10 through the following reaction:

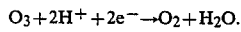

$$O_3 + 2H^+ + 2e^- \rightarrow O_2 + H_2O.$$

The water content (H$_2$O) is oxidized on the counter electrode 12 through the following reaction:

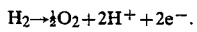

$$H_2 \rightarrow \tfrac{1}{2}O_2 + 2H^+ + 2e^-.$$

Thus the following reaction takes place as a whole:

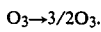

$$O_3 \rightarrow 3/2 O_2.$$

Ozone gas concentration is determined at this time by measuring electrolytic current flowing in proportion to the ozone gas concentration.

The catalyzer 6 should preferably comprise manganese dioxide (MnO$_2$), cupric oxide (CuO) or the like.

It is necessary for the ozone gas removal confirming gas sensor 7' to reliably detect low concentration ozone gas in particular. It is therefore preferable to use the semiconductor type gas sensor therefor.

With the suction type ozone gas detecting device having the foregoing construction, ozone gas in the gas being detected is reduced to oxygen gas having a low oxidizing ability during passage through the catalyzer after the ozone gas measuring sensor. Ozone gas is thus prevented from being drawn into the suction pump.

Where the suction pump is disposed immediately downstream of the catalyzer, there is a danger of ozone gas being drawn into the suction pump when the reducing capacity of the catalyzer diminishes or when ozone gas passes through the catalyzer in an amount exceeding the reducing capacity thereof. According to the present invention, however, the automatic control unit is operable to automatically stop the gas drawing operation of the suction pump when the ozone gas removal confirming sensor gives a detection result that ozone gas remains in the gas having passed through the catalyzer in an amount exceeding a predetermined level. Consequently, the gas is neither drawn into the suction pump nor released to ambient air on such an occasion.

It is conceivable to use an oxidation resistant material for a conventional suction pump. Such a measure, however, would be more costly than providing the catalyzer, ozone gas removal confirming gas sensor, and automatic control unit as in the present invention. Moreover, such a measure would result in the disadvantage of endangering people through exposure to the gas released from the suction pump to the ambient. By contrast, the present invention allows the suction pump to be used reliably over a long period, thereby providing ozone gas detecting devices having excellent utility and economy.

What is claimed is:

1. An ozone gas sensor comprising a film type semiconductor element including a substrate and a semiconductor film consisting of a metallic oxide formed on the substrate, and a layer of silica formed on a surface of the film type semiconductor element, wherein at least one thin film layer selected from metals and metal oxides is interposed between said semiconductor film and said layer of silica.

2. An ozone gas sensor as claimed in claim 1, wherein the metal forming said thin film layer comprises a transition metal.

3. An ozone gas sensor as claimed in claim 1 or 2, wherein said semiconductor film (18b) comprises at least indium oxide (In$_2$O$_3$).

4. An ozone gas detecting device comprising a sensor probe for contacting a gas to be detected and including an ozone gas sensor therein, and an indicator for indicating concentration of the gas detected, wherein said ozone gas sensor comprises a film type semiconductor element including a substrate and a semiconductor film consisting of a metallic oxide formed on the substrate, a layer of silica formed on a surface of the film type semiconductor element, and at least one thin film layer selected from metals and metal oxides and interposed between said semiconductor film and said layer of silica.

5. An ozone gas detecting device as claimed in claim 4, wherein the metal forming said thin film layer comprises a transition metal.

6. An ozone gas detecting device as claimed in claim 4 or 5, wherein said semiconductor film comprises at least indium oxide (In$_2$O$_3$).

7. An ozone gas detecting device comprising an ozone gas sensor mounted on a gas intake passage (R)

connected to a suction pump for detecting ozone gas concentration in a gas being measured, a catalyzer mounted between said ozone gas sensor and said suction pump for reducing ozone gas to oxygen gas, an ozone gas removal confirming gas sensor mounted on said gas intake passage downstream of said catalyzer, and automatic control means for automatically stopping a gas drawing operation of said suction pump only when said ozone gas removal confirming sensor gives a detection result that ozone gas remains in the gas having passed through said catalyzer in an amount exceeding a predetermined level, wherein said ozone gas removal confirming gas sensor comprises a film type semiconductor element including a substrate and a semiconductor film consisting of a metallic oxide formed on the substrate, a layer of silica formed on a surface of the film type semiconductor element, and at least one thin film layer selected from metals and metal oxides and interposed between said semiconductor film and said layer of silica.

8. An ozone gas detecting device as claimed in claim 7, wherein the metal forming said thin film layer comprises a transition metal.

9. An ozone gas detecting device as claimed in claim 7 or 8, wherein said semiconductor film comprises at least indium oxide ($In_2O_3$).

* * * * *